US010034662B2

(12) United States Patent
Bass et al.

(10) Patent No.: US 10,034,662 B2
(45) Date of Patent: Jul. 31, 2018

(54) SURGICAL RETRACTOR WITH A LOCKING RETRACTOR BLADE AND SWIVEL SIDE ARMS

(71) Applicant: TEDAN SURGICAL INNOVATIONS, LLC., Sugarland, TX (US)

(72) Inventors: Daniel Bass, Half Moon Bay, CA (US); Adam Young, Redwood City, CA (US)

(73) Assignee: TEDAN SURGICAL INNOVATIONS, LLC., Sugarland, TX (US)

( * ) Notice: Subject to any disclaimer, the term of this patent is extended or adjusted under 35 U.S.C. 154(b) by 0 days.

(21) Appl. No.: 15/450,804

(22) Filed: Mar. 6, 2017

(65) Prior Publication Data

US 2017/0172556 A1 Jun. 22, 2017

Related U.S. Application Data

(63) Continuation-in-part of application No. 14/447,924, filed on Jul. 31, 2014, now Pat. No. 9,636,097.

(51) Int. Cl.
*A61B 1/32* (2006.01)
*A61B 17/02* (2006.01)

(52) U.S. Cl.
CPC .................. *A61B 17/0206* (2013.01)

(58) Field of Classification Search
CPC .................. A61B 17/02–17/0293; A61B 2017/0212–2017/0287
USPC .................. 606/200–248
See application file for complete search history.

(56) References Cited

U.S. PATENT DOCUMENTS

| 1,607,788 | A | 11/1926 | Atkinson |
| 3,119,594 | A | 1/1964 | Heggem |
| 3,737,142 | A | 6/1973 | Boswell et al. |
| 4,976,403 | A | 12/1990 | Bramblet |
| 5,902,233 | A | 5/1999 | Farley et al. |
| 7,182,729 | B2 | 2/2007 | Abdelgany et al. |
| 7,758,501 | B2 | 7/2010 | Frasier |
| 7,850,608 | B2 | 12/2010 | Hamada |
| 7,887,482 | B2 | 2/2011 | Hamada |
| 7,922,658 | B2 | 4/2011 | Cohen et al. |
| 7,931,589 | B2 | 4/2011 | Cohen et al. |
| 7,935,054 | B2 | 5/2011 | Hamada |
| 7,946,982 | B2 | 5/2011 | Hamada |
| 7,988,625 | B2 | 8/2011 | Abdelgany et al. |

(Continued)

*Primary Examiner* — Matthew Lawson
(74) *Attorney, Agent, or Firm* — Kramer Amado, P.C.

(57) ABSTRACT

A surgical retractor including a retractor body, and a retractor arm, a control assembly configured to control movement of the retractor blade, the control assembly including a base member having an opening, a regulating member configured to control rotation of a first portion of the retractor arm and move through the opening of the base member, a connecting member cooperatively connected to the regulating member, and a barrel assembly in operative slidable engagement with the opening formed in the base member, wherein rotation of the regulating member in a selected direction moves a stem of the regulating member through the opening thereby forcing the barrel assembly to slide along the opening and the base member to pivot relative to a second portion of the retractor arm between a first position and second position.

20 Claims, 7 Drawing Sheets

(56) References Cited

U.S. PATENT DOCUMENTS

| | | | |
|---|---|---|---|
| 8,257,255 | B2 | 9/2012 | Farley et al. |
| 8,298,139 | B2 | 10/2012 | Hamada |
| 8,303,499 | B2 | 11/2012 | Hamada |
| 8,357,184 | B2 | 1/2013 | Woolley et al. |
| 8,360,971 | B2 | 1/2013 | Farley et al. |
| 8,435,269 | B2 | 5/2013 | Woolley et al. |
| 8,535,320 | B2 | 9/2013 | Woolley et al. |
| 8,636,656 | B2 | 1/2014 | Nichter et al. |
| 8,727,975 | B1 | 5/2014 | Pfabe |
| 2004/0193018 | A1 | 9/2004 | Thalgott |
| 2007/0038033 | A1 | 2/2007 | Jones |
| 2007/0208228 | A1 | 9/2007 | Pavento |
| 2011/0301422 | A1 | 12/2011 | Woolley et al. |
| 2012/0245431 | A1* | 9/2012 | Baudouin .......... A61B 17/0206 600/213 |
| 2014/0018633 | A1 | 1/2014 | Woolley et al. |
| 2014/0114137 | A1 | 4/2014 | Reglos et al. |

\* cited by examiner

SURGICAL RETRACTOR WITH A LOCKING RETRACTOR BLADE AND SWIVEL SIDE ARMS

CROSS-REFERENCE TO RELATED APPLICATIONS

This application is a continuation-in-part Application of U.S. patent application Ser. No. 14/447,924, filed Jul. 31, 2014.

TECHNICAL FIELD

The invention relates to a surgical retractor, and more particularly relates to a surgical retractor having a control assembly configured for facilitating reciprocating movement, as well as locking a retractor blade in a selected position.

BACKGROUND

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades may be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

The retractors in use today retract the opening created in the body of the patient in a uniform manner. If the surgeon needs a large opening near the spine, for instance, the opening in the body of the patient must be retracted in a uniform manner. This creates significant trauma for the patient and increases the patient's recovery time.

SUMMARY

A brief summary of various embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

According to one embodiment, there is provided a surgical retractor including a retractor body, and a retractor arm including a first portion configured to operatively connect to a retractor blade and a second portion configured to operatively connect to the retractor body, a control assembly configured to control movement of the retractor blade, the control assembly including a base member having an opening and movable between a first position and second position, a regulating member configured to control rotation of the first portion of the retractor arm and move through the opening of the base member, a connecting member cooperatively connected to the regulating member, and a barrel assembly in operative slidable engagement with the opening formed in the base member, wherein rotation of the regulating member in a selected direction moves a stem of the regulating member through the opening thereby forcing the barrel assembly to slide along the opening and the base member to pivot relative to the second portion of the retractor arm between a first position and second position.

The opening may include a first slot and a second slot.

The barrel assembly may include a plurality of protrusions and a plurality of sliding members.

The regulating member and connecting member may be threadably engaged such that rotation of the regulating member forces the stem of the regulating member to move through the first opening, from a first position to a second position.

The surgical retractor may include a second retractor arm mounted opposite the retractor arm to rotate in opposite direction of the retractor arm. Rotational movement of the base member may force the barrels assembly to rotate relative to the retractor arm.

The barrel assembly may rotate and slide within the opening.

The surgical retractor may include a connecting pin to connect the first portion to the second portion. The first portion may rotate about the connecting pin.

The second portion may include an opening to receive the regulating member.

The regulating member may include a wide stem portion and a narrow stem portion.

The regulating member may have a series of external threads configured to operatively engage a connecting member having internal threads.

The barrel member may have an opening formed therein configured to receive the stem therethrough.

The barrel assembly may include dual slidable members formed on opposing sides of the barrel member. The dual slidable members may have a generally cylindrical shape facilitating rotational movement within the opening of the base member.

BRIEF DESCRIPTION OF THE DRAWINGS

Examples of the invention are illustrated, without limitation, in the accompanying figures in which like numeral references refer to like elements and wherein.

To facilitate understanding, identical reference numerals have been used to designate elements having substantially the same or similar structure and/or substantially the same or similar function

DETAILED DESCRIPTION

For simplicity and illustrative purposes, the principles are shown by way of examples of systems and methods described. In the following description, numerous specific details are set forth in order to provide a thorough understanding of the examples. It will be apparent however, to one of ordinary skill in the art, that the examples may be practiced without limitation to these specific details. In other instances, well known methods and structures are not described in detail so as not to unnecessarily obscure understanding of the examples.

One common problem with conventional retractors and the connected retractor blades, are that when the retractor blades are extended from the retractor body, the retractor blades move relatively "freely" when engaged with a body member and do not lock into a selected position. This can be problematic, as most surgical procedures require the surgeon to perform with detail and precision. As such, retractor blades that move freely while a surgeon is attempting to perform a procedure can be distracting, and potentially cause the doctor to make a mistake while performing a procedure on a patient.

The foregoing advantages of the invention are improvements of those that can be achieved by the various exemplary embodiments and are not intended to be exhaustive or limiting of the possible advantages which can be realized. Thus, these and other advantages of the various exemplary embodiments will be apparent from the description herein or can be learned from practicing the various exemplary embodiments, both as embodied herein or as modified in view of any variation that may be apparent to those skilled in the art. Accordingly, the invention resides in the novel methods, arrangements, combinations, and improvements herein shown and described in various exemplary embodiments.

Retractors generally provide retractor arms that are adjustable. The retractor arms extend generally outward from the retractor body and may be configured to rotate and/or move in several different directions. As such, it is common that the retractor arms may move relatively freely until they are inserted and adjusted to apply force to the body member(s). The unpredictable movement and/or "play" of the retractor arms can be a distracting to the user during a surgical procedure. Accordingly, it is desirable to provide a surgical retractor including a lockable retractor assembly with one or more retractor arms that may be locked in a selected position, eliminating unnecessary movement of the retractor arms during usage and providing the doctor controlled precision during use of the retractor.

Figure 1:
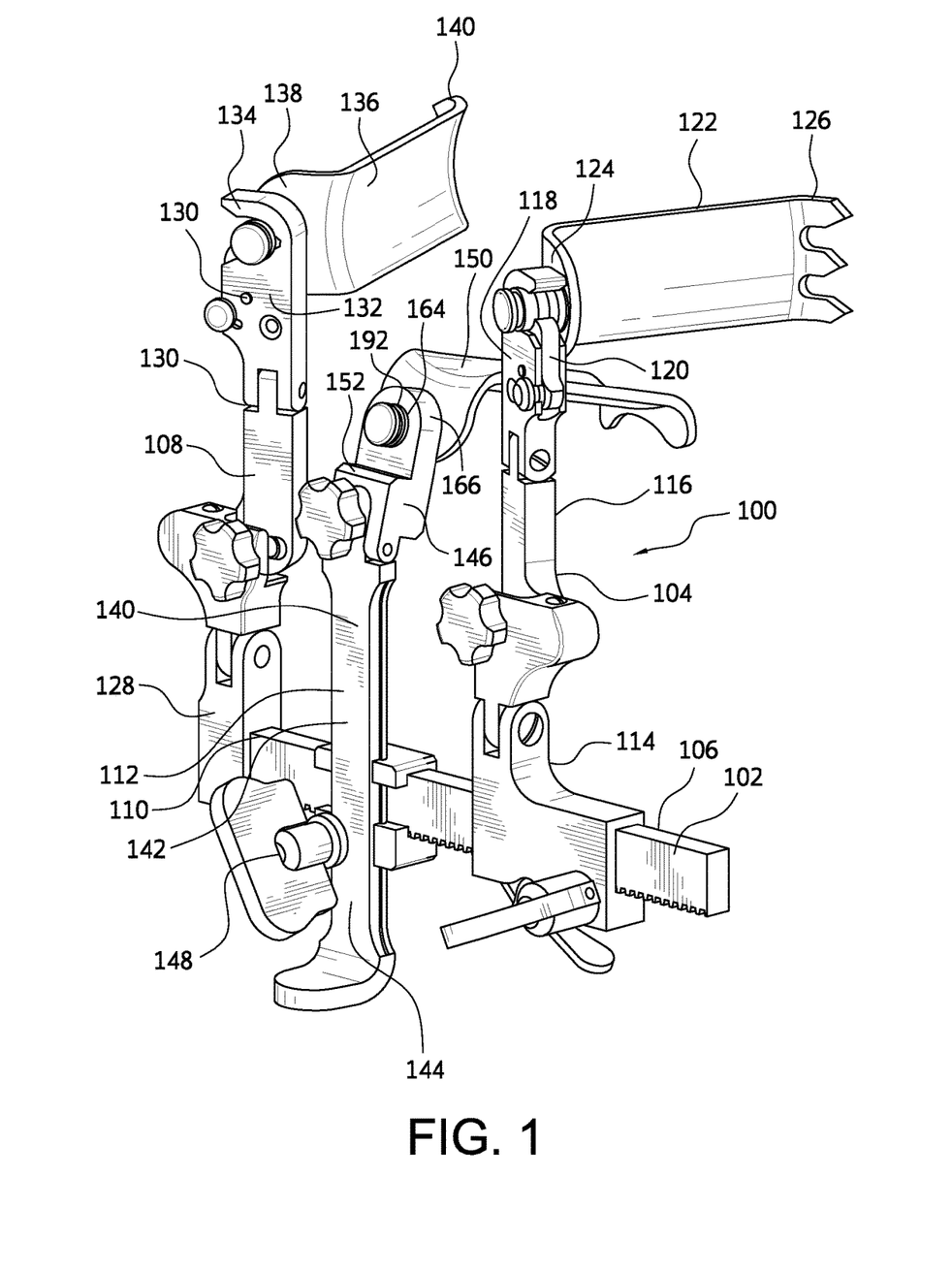
FIG. 1 shows a perspective diagram of an exemplary surgical retractor with rotating blades and a locking third retractor assembly, in accordance with the present invention.

Referring now to the drawings, wherein the illustrations are for purposes of describing one or more embodiments and not for the purposes of limiting the same, FIG. 1 illustrates an embodiment of the surgical retractor generally designated by the reference numeral 100. The surgical retractor 100 includes a retractor body 102, a first retractor arm 104 operatively connected to the retractor body 102 at a first end 106 of the retractor body 102, a second retractor arm 108 operatively connected to a second end 110 of the retractor body 102, and a retractor arm 112, which may be referred to as a third retractor arm 112, operatively connected to the retractor body 102, generally intermediate to the first retractor arm 104 and second retractor arm 108. The first retractor arm 104 generally includes a first portion 114 and a second portion 116. The first retractor arm 104 is connected to the retractor body 102 by the first portion 114. The second portion 116 of the first retractor arm 104 is operatively connected to the first portion 114, and includes at a distal end 118 having a connector 120. The connector 120 is configured to receive a retractor blade 122. Notably, it is contemplated that the connector 120 may be configured for use in a variety of manners. One example of a connector 120 for use with a surgical retractor blade 122 is described in U.S. Pat. No. 7,537,565 by Daniel Bass and entitled "Surgical Retractor with Rotating Blades". This application is hereby incorporated by reference for all purposes in its entirety.

The retractor blade 122 includes a proximal end 124 provided generally proximate to the connector 120 and a distal end 126 which is configured for insertion into the body of a patient. The second portion 116, which retains the retractor blade 122 may rotate generally around an axis parallel to a line drawn along a length of the retractor arm 104 as described herein. This rotation may cause the distal end 126 of the retractor blade 122 to tilt or angle thus exposing a larger area inside the body of a patient without significantly increasing an insertion point. Because the distal end 118 of the retractor blade 122 moves through a larger range of motion than the proximal end 114, the insertion point may be smaller than the area inside the body of the patient.

The second retractor arm 108 includes a first portion 128 connecting the second retractor arm 108 and a second portion 130 connected to the retractor body 102 by the first portion 128. Similar to the first retractor arm 104, the second portion 130 of the second retractor arm 108 may be rotatably attached to the first portion 128 and may include at a distal end 132 including a connector 134 for receiving a second retractor blade 136. The second retractor blade 136 may include a proximal end 138 near the connector 134 and a distal end 140 which may also be inserted into the body of a patient. Similar to the first retractor arm 104, the second portion 130 of the second retractor arm 108 receives the second retractor blade 136 and may rotate around an axis parallel to a line drawn along a length of the retractor arm 108 as described herein. This rotation causes the distal end 140 of the retractor blade 136 to tilt or angle thus exposing a larger area inside the body of a patient without significantly increasing an insertion point. Because the distal end 140 of the retractor blade 136 moves through a larger range of motion than the proximal end 138, the insertion point may be smaller than the area inside the body of the patient.

When the retractor blades 122 and 136 are inserted into the body of a patient, the second portions 116 and 130 of the respective first retractor arm 104 and second retractor arm 108 may be rotated by a user operating the retractor assembly. Rotation of the second portions 116 and 130 forces the respective distal ends 126 and 140 to separate and expose a larger area inside the body of the patient than the area of the insertion point. The proximal ends 124 and 138 of the retractor blades 122 and 136 may lie near the insertion point but may not significantly increase the insertion area as the proximal ends 124 and 138 move through a smaller range of motion than the distal ends 126 and 140 of the retractor blades 122 and 136.

The retractor arm 112 generally includes a first portion 142 connected to the retractor body 102, a second or lower portion 144, and a third portion 140 connected to a retractor blade 150, which may be referred to as a third retractor blade 150. The third retractor blade 150 is operatively connected to a connector 146 which also may be a control assembly 146 configured to control rotational movement of the retractor arm 112. As shown, the first portion 142 of the retractor arm 112 is adjustably connected to the retractor body 102 and may be raised and lowered relative to the retractor body 102 via a clamping member 148.

As shown, the lower portion 144 of the retractor arm 112 is insertable in the clamping member 148, thereby permitting movement of the retractor arm 112 to be raised and/or lowered relative to the body 102. The retractor arm 112 further includes a retractor blade 150, which may be connected to the control assembly 146 at an aperture 192 formed in the retractor 112. As such, reciprocating movement of the retractor blade 150 may be controlled by adjusting the control assembly 146. Notably, it is contemplated that the control assembly 146 may be provided in combination with the first retractor arm 104 and/or second retractor arm 108, to control rotational movement of the respective retractor blades 122 and 136. As shown, the third retractor arm 112 may be positioned on the retractor body 102 generally intermediate to the first retractor arm 104 and second retractor arm 108.

Figure 2A:
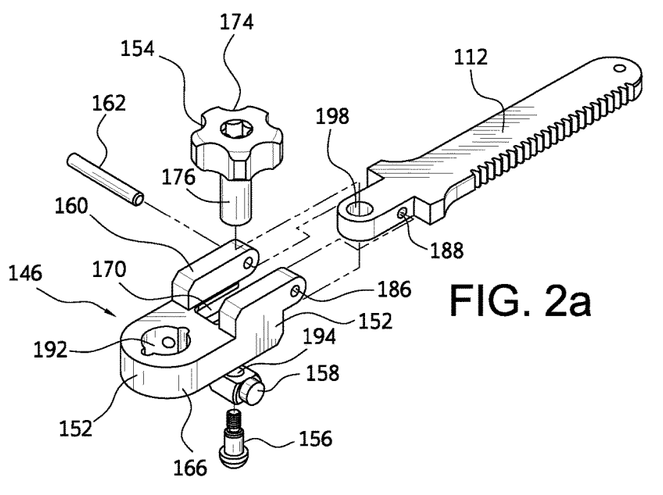
FIG. 2a shows an exploded top perspective view of the locking third retractor assembly of FIG. 1, illustrating a third retractor body connection to a base member.
Figure 2B:
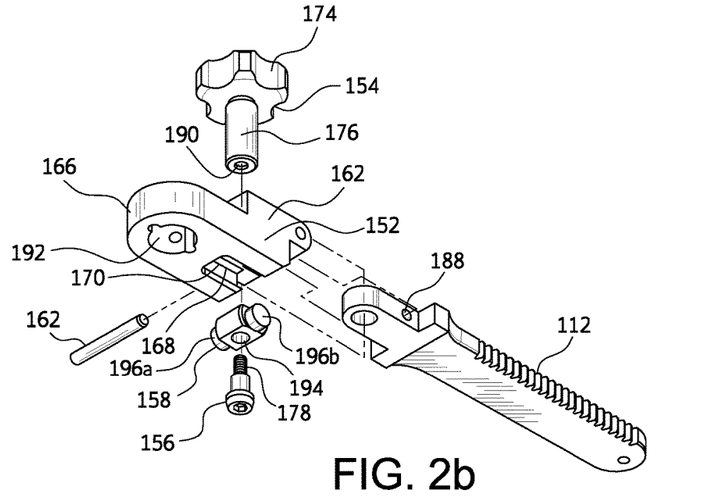
FIG. 2b shows an exploded bottom perspective view of the locking third retractor assembly of FIG. 1, illustrating a barrel operative relationship with a base member.

Continuing now to FIGS. 2a and 2b, there is an exploded illustration of the retractor arm 112 and control assembly 146 are shown. The control assembly 146 is configured to facilitate locking controlled movement of the third retractor blade 150, permitting a user to rotate and subsequently lock the retractor blade 150 into a selected position. As shown, the control assembly 146 includes a base member 152 having a first portion 160 configured for connection to the third retractor blade 150 and a second portion 166, configured to receive the retractor arm 112.

In addition to the base member 152, the control assembly 146 further includes a regulating member 154 adapted to control the reciprocating rotational movement the base member 152 in conjunction with the connected retractor blade 150. The base member 152 further includes a connecting member 156 or fastener, configured to cooperatively engage the regulating member 154, a connecting pin 162 insertable through an opening 188 formed in the third retractor arm 112 and an opening 186 formed in the base member 152, respectively. As such, the combination of the connecting pin 162, a reciprocating base member 152 and regulating member 154 provide a pivotal connection therebetween. The control assembly 146 further includes a barrel member 158 configured to be slidably positioned within the base member 152 and provided generally intermediate to the regulating member 154 and connecting member 156.

As shown in FIGS. 1, 2a and 2b the base member 152 includes a second portion 166 having an second opening or aperture 192 formed therein configured to receive an extension 164 of the third retractor blade 150, and a first portion 160 configured to receive a portion of the retractor arm 112. As shown, the aperture 192 of the base member 152 facilitates connection between the threaded extension 164 of the retractor blade 150 and the base member 152.

As shown in FIGS. 2a and 2b, the second portion 166 includes a second opening or slot 168 formed generally laterally therein, and configured to receive the barrel member 158. The second opening 168 or slot is dimensioned to facilitate slidable movement of the barrel member 158, between a first position and a second position, which facilitates rotational movement of the retractor arm 108. The base member 152 further includes a first opening 170, extending generally through the first portion 160 and second portion 166 of the base member 152 formed therein to receive a stem 176 or sleeve of the regulating member 154.

Figure 3:
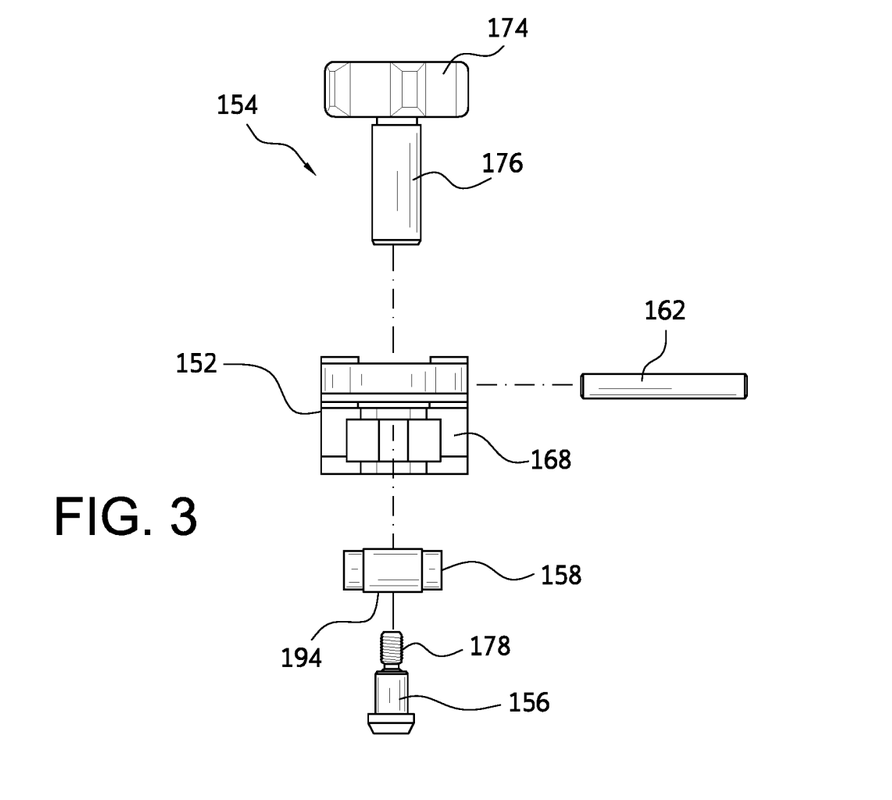
FIG. 3 is an exploded frontal view of the base member.
Figure 4:
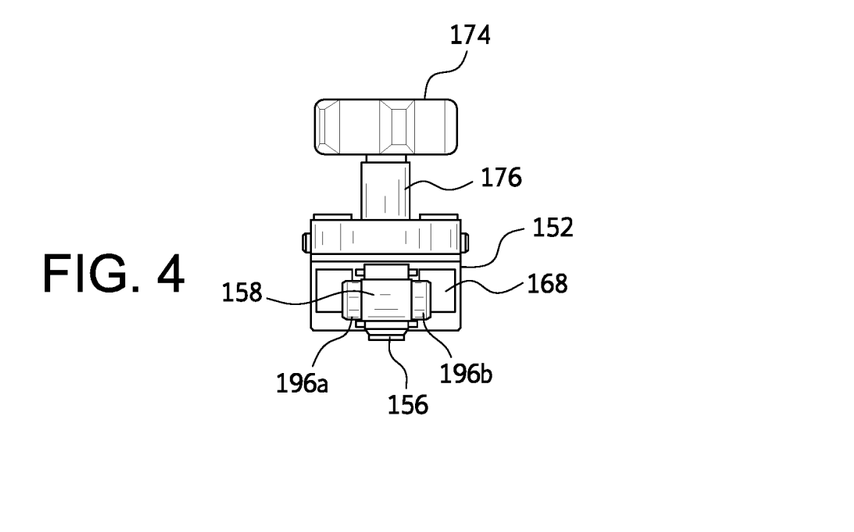
FIG. 4 is a frontal view of the base member of the third retractor assembly.

The barrel member 158 further includes a dual sliding members 196a and 196b having a generally cylindrical configuration to facilitate slidable movement about the second opening 168. As shown in FIGS. 3 and 4, the barrel member 158 has an aperture 194 formed therein, configured to receive the connecting member 156 therethrough As shown, the sliding members 196a-b extend from the body of the barrel member 158 in generally opposing directions to provide controlled sliding movement within.

The stem 176 of the regulating member 154 extends generally outward from the knob 174 and is configured to slide through the first opening 170 of the base member and an opening 198 formed in the retractor arm 112. As such the stem 176 operatively engages the connecting member 156 fastener. As shown, knob 174 is formed generally at the distal end of the regulating member 154, facilitating manual adjustment by a user with his/her hands. As shown in FIG. 2b, the stem 176 includes an opening 190 formed generally at the end of the stem and extending generally therein and configured to receivably engage the connecting member 156. The opening 190 may include inner threads to receive the connecting member 156. As shown in FIG. 3, the connecting member 156 including a series of outer threads 178, configured to cooperatively engage inner threads provided in the opening 190 of the stem 176.

The connecting member 156 extends through the barrel member 158 into the opening 190 formed in the stem 176.

Accordingly, the regulating member 154 and connecting member 156 are threadably engaged, such that rotation of the regulating member 154 forces the connecting member 156 to move towards or away from the stem 176 through the opening 190, thereby forcing the stem 176 of the regulating member 154 to move laterally through the opening 170 between a first position to a second position. In operation, the third retractor arm 150 may be moved between a first position and second position and locked in a selected position.

Figure 5:
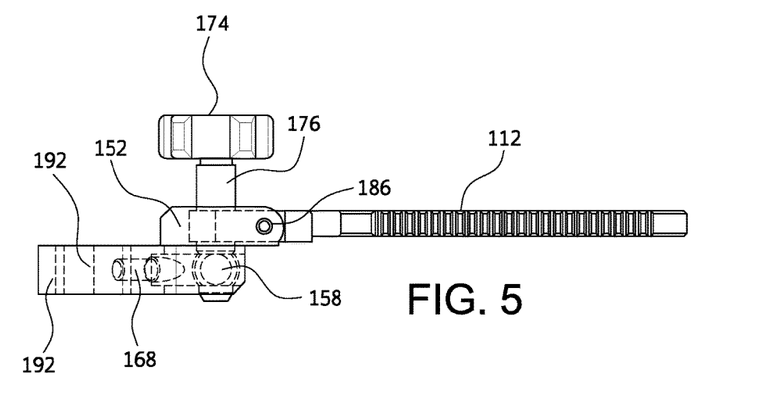
FIG. 5 is a side view of the locking retractor assembly illustrating the retractor assembly in a first position.
Figure 6:
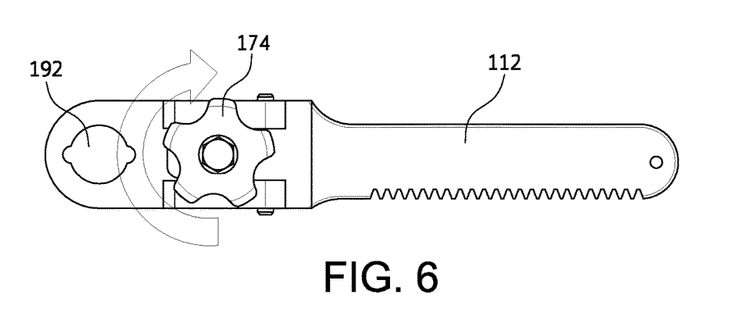
FIG. 6 is a top plan view of the third locking retractor assembly illustrating the retractor assembly in a first position.

As shown in FIG. 5, in a first position, the regulating member 154 and stem 176 are in a generally open extended position, extending away from the arm 112. As shown in FIG. 6, rotation of the regulating member 154 and threaded engagement with the connecting member 156 forces the regulating member 154 and stem 176 to move through the opening 170 as the regulating member 154 is rotated. The regulating member 154 and stem 176 move in a direction generally perpendicular relative to the axis of the third retractor arm 112, through the first opening, from a first position to a second position As the connecting member 156 is drawn through the opening 170 movement of the stem 176 forces the barrel member 158 to slide along the second opening 168.

Figure 7:
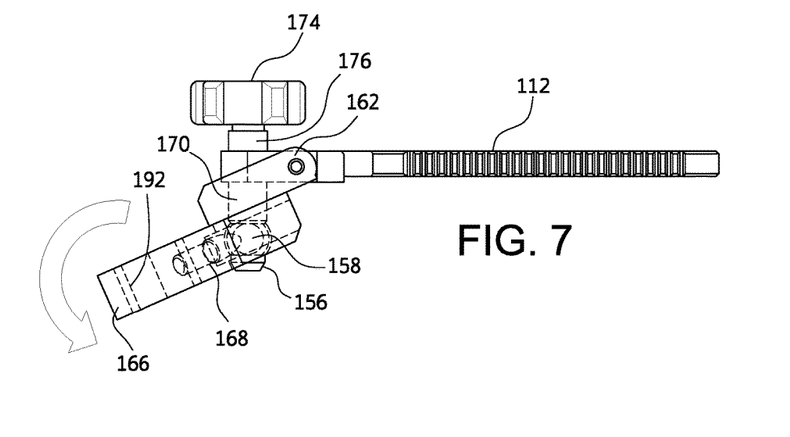
FIG. 7 is a side view of the locking retractor assembly illustrating the retractor assembly in a second position.

As shown the connecting pin 162 is inserted through an opening 188 formed in the retractor arm 112 and an opening 186 formed in the base member 152. Movement of the barrel member 158 along the opening 168 provides a force, biasing the base member 152 to pivot about the connecting pin 162 in a first direction. As shown in FIG. 7, as the base member 152 pivots or rotates, the second portion 166 of the base member 152 forces the retractor blade to rotate as shown in FIG. 7. Movement of the stem 176 of the regulating member 154 through the base member 152 between a first position to a second position forces the barrel member 158 to slide along the slot 168 from a first position to a second position thereby rotating the base member 152 and connected third retractor blade. As such, the forces applied by the stem 176 in cooperation with the connecting pin 162 lock the retractor blade 150 in a selected position.

Conversely, rotation of the regulating member 154 in an opposing direction causes the connecting member 156 to retreat from the stem 176 and forces the base member 152 to pivot about the connecting pin 162 in a second direction. As such, the retractor blade 150 is moved towards the retractor arm 112.

Figure 8A:
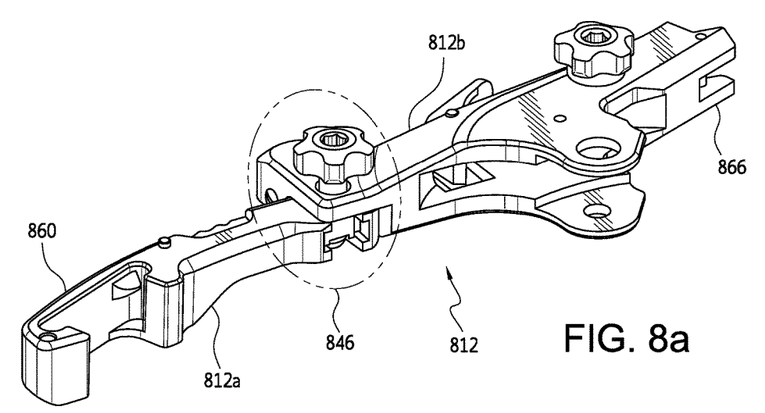
FIGS. 8a and 8b illustrate perspective views of a top side and a bottom side of a retractor arm in accordance with embodiments described herein.
Figure 8B:
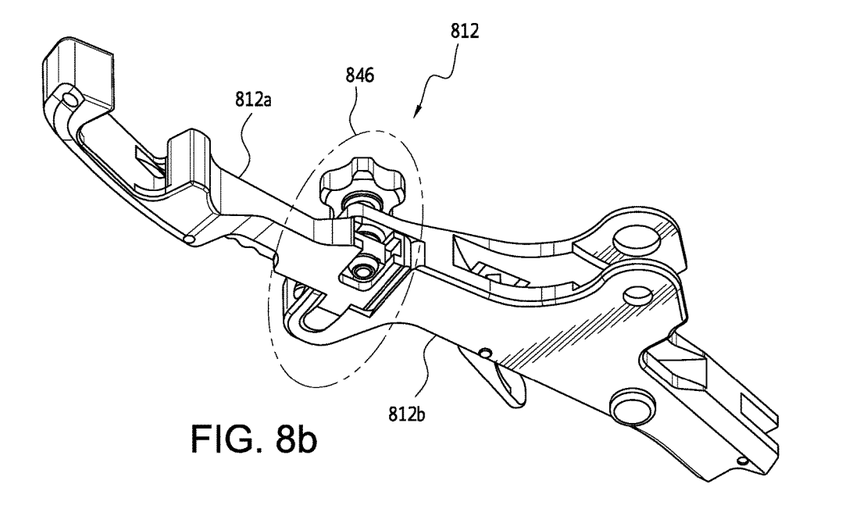

FIGS. 8a and 8b illustrate perspective views of a top side and a bottom side of a retractor arm 812 in accordance with embodiments described herein. Retractor arm 812 may be an example of retractors arms 104 and 108 illustrated in FIG. 1. One orientation of a retractor arm 812 may represent a retractor arm 104 and a reflection of the retractor arm 812 may be used as an embodiment of retractor arm 108 on an opposite side of a retractor assembly. Thus two retractor arms 812 may be used in the manner illustrated in FIG. 1 and rotate in opposing directions. FIGS. 8a and 8b illustrate a control assembly 846 that is configured to facilitate locking controlled movement of a retractor blade (not illustrated) by a holding member 860, permitting a user to rotate a first portion 812a of the retractor arm 812 and subsequently lock a retractor blade into a selected position. A second portion 812b of the retractor arm 812 includes a mounting section 866 in which the retractor arm 812 may be attached to a retractor body such as retractor body 102 illustrated in FIG. 1.

Figure 9A:
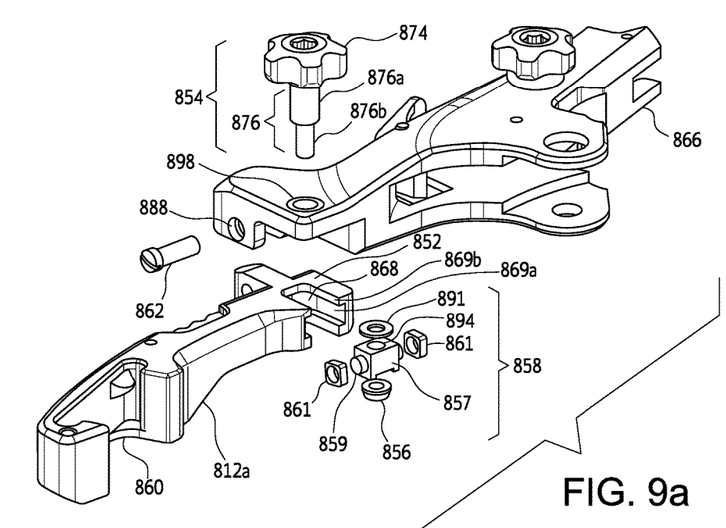
FIGS. 9a and 9b illustrate exploded views of a top side and a bottom side of a retractor arm and control assembly in accordance with FIG. 8.
Figure 9B:
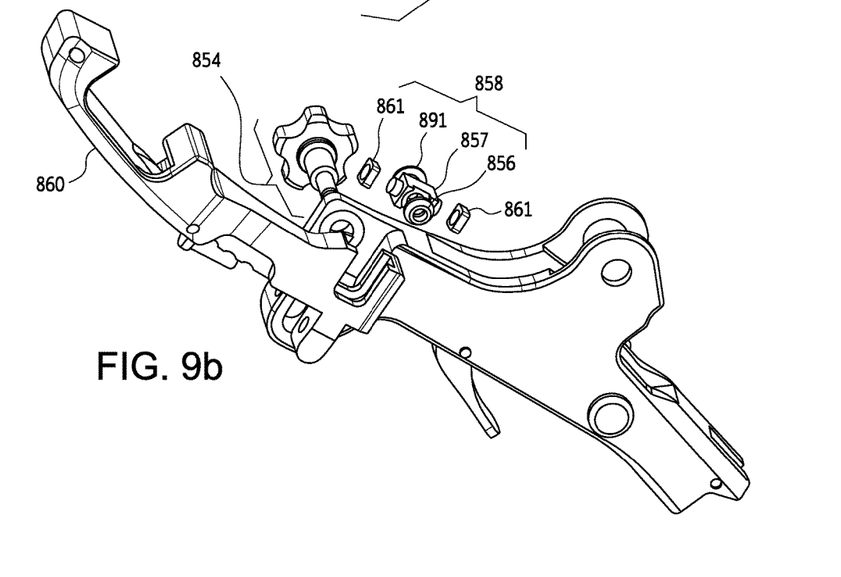

FIGS. 9a and 9b illustrate exploded views of a top side and a bottom side of a retractor arm 812 and control assembly 846 in accordance with FIG. 8. The control assembly 846 may include several interworking parts in an area where the first portion 812a and second portion 812b of the retractor arm 812 intersect. The control assembly 846 may include a knob 874, a first or wide stem member 876a, a second or narrow stem member 876b, a barrel assembly 858, and a rotating pin 862. The wide stem member 876a, narrow stem member 876b, knob 874, and other interlocking parts of these components are referred to as a regulating member 854. The regulating member 854 is adapted to control rotational movement of a base member 852 of the first portion 812a in relation to the second portion 812b of the retractor arm 812.

The control assembly may include a rotating pin 862. In order to rotate the first portion 812a of the retractor arm 812 in relation to the second portion 812b, the rotating pin 862 of the control assembly 846 may be inserted into an opening 888 in the second portion 812b of the retractor arm 812 to create a rotating axis for the first portion 812a. The control assembly 846 allows the first portion 812a of the retractor arm 812 to rotate relative to the second portion 812b of the retractor arm 812 about the rotating pin 862. When the first portion 812a is connected to the second portion 812b by the control assembly 846, rotation of the regulating member 854 pushes or pulls the base member 852 away from or towards the second portion 812b of the retractor arm 812, establishing a pivot point in the retractor arm 812 about the rotating axis.

The control assembly 846 further includes a barrel assembly 858 configured to be slidably positioned within an opening 868 of the base member 852. The barrel assembly 858 includes a connecting member 856 or fastener, configured to cooperatively engage the regulating member 854.

As illustrated in FIGS. 9a and 9b, the base member 852 includes an opening 868 having an outer or first slot 869a and an inner or second slot 869b formed generally laterally therein, and configured to receive the barrel assembly 858. The slots 869a and 869b within the base member 852 extend in a continuous manner having three sides within the base member 852. The three sides permit the barrel assembly 858 to be inserted into the base member 852, slide and rotate within the base member 852, and be held firmly in place by parts of the barrel assembly 858.

The barrel assembly 858 includes a base member 857 and opposing protrusions or knobs 859 extending from alternate sides of the base member 857. The protrusions 859 permit the barrel assembly 858 to rotate within the opening 868, and rotate the first portion 812a relative to the second portion 812b. The barrel assembly 858 further includes sliding members 861 to interface with the inner slots 869b. Before being inserted into the opening 868, the protrusions 859 are coupled to the sliding members 861 in a rotatable manner.

The coupling of the protrusions 859 to the sliding members 861 may not include any adhesive or property which could prevent rotational movement of the barrel assembly 858. The barrel assembly 858 including a washer 891, fastener 856, barrel 857, protrusions 859, and sliding members 861 are inserted into the base member 852 of the first portion 812a of the retractor arm 812. Shapes of the protrusions 859 and insides of the sliding members 861 may be round or circular to allow the barrel assembly 858 to rotate within the opening 868. In other embodiments the sliding members 861 may be omitted. The fastener 856 may receive the second stem member 876b through the barrel member 857. The second stem member 876b may be threaded on an outer portion thereof. The fastener 856 may be threaded on inside portions thereof to receive and securely hold the second stem member 876b. In other embodiments, the second stem member 876b may have an internally threaded opening that accepts a threaded portion of the fasten 856 (see outer threads 178 and opening 190 in FIG. 2B). On an opposite side of the barrel member 858 is the washer 891. The washer 891 may be mounted to the barrel member 858 and provide a secure or snug fit within the opening 868. In other embodiments the washer may be omitted.

The opening 868 and slots 869a-b are dimensioned to facilitate rotatable movement and slidable movement of the barrel assembly 858 through multiple positions to facilitate rotational movement of the first portion 812a of the retractor arm 812 in relation to the second portion 812b of the retractor arm 812. As shown, the protrusions 859a-b extend from the body of the barrel member 857 in generally opposing directions to provide in combination with the sliding members 861, controlled sliding movement within the inner slot 869b of the opening 868.

As illustrated in FIGS. 9a and 9b, the barrel member 857 has an aperture 894 formed therein, configured to receive the second part 876b of the stem 876 therethrough. The stem 876 of the regulating member 854 extends generally outward from the knob 874 and is configured to slide through the opening 868 of the base member 852 and to move through an the threaded opening 898 formed in the second portion 812b of the retractor arm 812. Thus the upper stem portion 876a may be threaded to engage with the threads of the opening 898. As shown, knob 874 is formed generally at the distal end of the regulating member 854, facilitating manual adjustment by a user with his/her hands.

When assembled, the barrel assembly 858 will sit within the base member 852 and the barrel assembly 858 is captured between the first part 876a of the stem member 876 and the fastener 856. In operation, when a user turns the knob 874 of the regulating member 854 in a clockwise direction, the first part 876a of the stem 876 turns within the opening 898 to cause the barrel 857 to rotate and slide within the slot 868 pushing the first portion 812a of the retractor arm 812 away from the second portion 812b. The threads of the various members may be oriented such that a counter-clockwise rotation of the knob 874 would also rotate the first and second portions relative to each other.

In another embodiment, the regulating member 854, barrel member 857, and fastener 856 may be threadably engaged, such that rotation of the regulating member 854 forces the barrel member 857 and fastener 856 to move towards or away from the knob 874 through the opening 868. By this rotational movement of the regulating member 854, the stem 876 of the barrel assembly 857 is forced to move laterally and rotationally through the opening 868 between different positions determined by the rotation of the knob 174. This action causes the base member 852 of the first portion 812a to rotate away from the second portion 812b, as illustrated in FIG. 10b. This allows the retractor arm 812 to have greater range of motion regarding retractor blades attached to the first portion 812a.

Figure 10A:
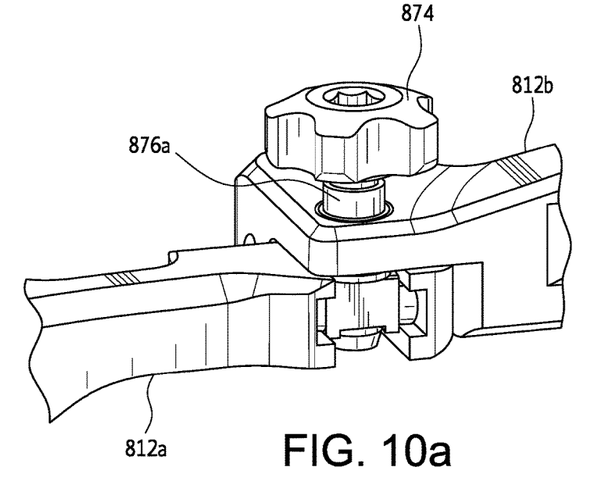
FIGS. 10a and 10b illustrate static and rotational positioning of a retractor arm in accordance with FIG. 8.
Figure 10B:
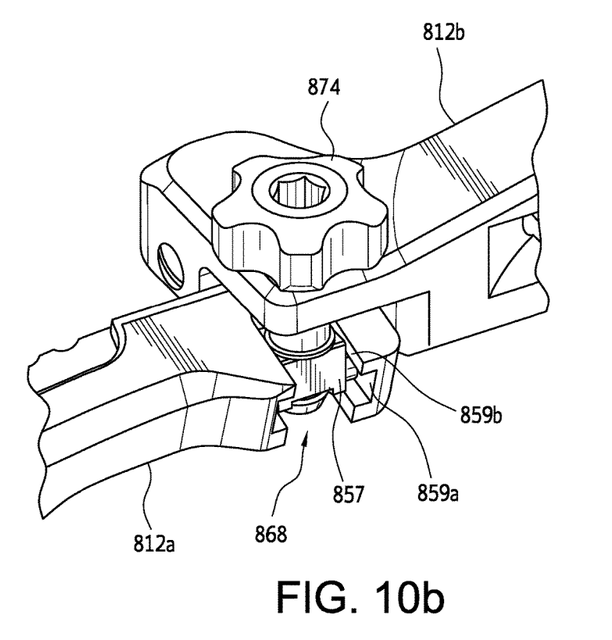

FIGS. 10a and 10b illustrate static and rotational positioning of a retractor arm in accordance with FIG. 8. As shown in FIG. 10a, in a first position, the regulating member 854 and stem 876 are in a generally open extended position, extending away from the second portion 812b of the retractor arm 812. As a result the first portion 812a and second portion 812b of the retractor arm 812 are generally aligned. As shown in FIG. 10b, rotation of the regulating member 854 and engagement with the connecting member 856 forces the regulating member 854 and stem 876 to move through the opening 868 as the regulating member 854 is rotated. The regulating member 854 and stem 876 move in a direction generally perpendicular relative to the axis of the second portion 812b of the retractor arm 812, through the opening 898, from a first position to a second position.

The fastener 856 is connected to the barrel member 857. As the stem 876 is rotated through the opening 898. As a result, the turning of the knob 874 then pushes the barrel assembly 858 along the opening 868 and the movement of the stem 876 forces the barrel assembly 858 to rotate in and slide along the opening 868. When rotating and sliding, only the sliding members 861 remain within the slot 869a. The remaining parts of the barrel assembly 858 including the barrel member 857, washer 891, and fastening member 856 rotate within the outer slot portion 869b of the slot 869. The barrel assembly 858 via the sliding members 861 rotates in and slides down the slot 869a.

As shown in FIGS. 10a and 10b, as the base member 852 pivots or rotates, the base member 152 forces the first portion 812a of the retractor arm, and thus a retractor blade (not illustrated) to rotate about the rotating pin 862. Movement of the stem 876 of the regulating member 854 through the base member 852 between a first position and a second position forces the barrel assembly 858 to slide along the slot 869 from a first position to a second position thereby rotating the base member 852 and connected retractor blade. As such, the forces applied by the stem 876 in cooperation with the threaded portions of the stem 876, fastener 856, and rotating pin 862 may lock the retractor blade in a selected position.

As illustrated in FIG. 10b, when the barrel assembly 858 rotates and slides in the opening 868, the barrel member 857 rotates relative to the sliding members 861. Because the sliding members 861 are rectangular and geometrically shaped to correspond to the shape of the slot 869, the sliding members 861 slide back in forth in the slot 869 depending on the direction the knob 874 is turned. The sliding members 861 sliding in the slot 869 may occur at the same time the protrusions 859 rotate in the sliding members 861.

As illustrated in FIG. 10b, the first portion 812a of the retractor arm 812 may be held in position by forces created by at least one of the tension between the first threaded stem section 876a and threaded opening 898, and between the movement of the sliding members 861 in the slots 869. In operation, the first portion 812a of the retractor arm 812 may be rotated relative to the second portion 812b of the retractor arm 812 and locked in a selected position Conversely, rotation of the regulating member 854 in an opposing direction causes the first portion 812a of the retractor arm 812 to rotate closer to the second portion 812b of the retractor arm 812 and forces the base member 852 to pivot about the connecting pin 862 in a second direction.

What has been described and illustrated herein are examples of the systems and methods described herein along with some of their variations. The terms, descriptions and figures used herein are set forth by way of illustration only and are not meant as limitations. Those skilled in the art will recognize that many variations are possible within the spirit and scope of these examples, which are intended to be defined by the following claims and their equivalents in which all terms are meant in their broadest reasonable sense unless otherwise indicated.

What is claimed is:

1. A surgical retractor comprising:
   a retractor body;

a retractor arm including a first portion configured to operatively connect to a retractor blade and a second portion configured to operatively connect to the retractor body; and a control assembly configured to control movement of the retractor blade, the control assembly including a base member of the first portion of the retractor arm having an opening and movable between a first position and second position, a regulating member configured to control rotation of the first portion of the retractor arm and move through the opening of the base member of the first portion of the retractor arm, a connecting member cooperatively connected to the regulating member, and a barrel assembly in operative slidable engagement with the opening formed in the base member of the first portion of the retractor arm, wherein rotation of the regulating member in a selected direction moves a stem of the regulating member through the opening thereby forcing the barrel assembly to laterally slide along the opening and the base member of the first portion of the retractor arm to pivot relative to the second portion of the retractor arm between a first position and second position.

2. The surgical retractor of claim 1, wherein the opening includes a first slot and a second slot.

3. The surgical retractor of claim 1, wherein the barrel assembly includes a plurality of protrusions and a plurality of sliding members.

4. The surgical retractor of claim 1, wherein the regulating member and connecting member are threadably engaged such that rotation of the regulating member forces the stem of the regulating member to move through the first opening, from a first position to a second position.

5. The surgical retractor of claim 1, comprising a second retractor arm mounted opposite the retractor arm to rotate in opposite direction of the retractor arm.

6. The surgical retractor of claim 1, wherein rotational movement of the base member of the first portion of the retractor arm forces the barrel assembly to rotate relative to the second portion of the retractor arm.

7. The surgical retractor of claim 1, wherein the barrel assembly rotates and slides within the opening.

8. The surgical retractor of claim 1, comprising a connecting pin to connect the first portion to the second portion.

9. The surgical retractor of claim 8, wherein the first portion rotates about the connecting pin.

10. The surgical retractor of claim 1, wherein the second portion includes an opening to receive the regulating member.

11. The surgical retractor of claim 1, wherein the regulating member includes a wide stem portion and a narrow stem portion.

12. The surgical retractor of claim 1, wherein the regulating member has a series of external threads configured to operatively engage the connecting member having internal threads.

13. The surgical retractor of claim 1, wherein the barrel member has an opening formed therein configured to receive the stem there through.

14. The surgical retractor of claim 13, wherein the barrel assembly includes dual slidable members formed on opposing sides of the barrel member.

15. The surgical retractor of claim 14, wherein the dual slidable members have a generally cylindrical shape facilitating rotational movement within the opening of the base member of the first portion of the retractor arm.

16. A surgical retractor comprising:

a retractor body;

a first portion of a retractor arm configured to operatively connect to a retractor blade, the first portion including a base member having an opening therein;

a second portion of the retractor arm configured to operatively connect to the retractor body, the second portion including a hole to receive a regulating member and a rotating pin opening;

a barrel member inserted within the base member of the first portion of the retractor arm to couple with a regulating member; and a regulating member operatively engaged with the first portion, the second portion, and the barrel member, wherein the regulating member is turned within the first portion and the second portion to force the barrel member to laterally slide within the opening and rotate the first portion of the retractor arm relative to the second portion of the retractor arm.

17. The surgical retractor of claim 16, wherein the barrel member includes protrusions extending therefrom.

18. The surgical retractor of claim 16, wherein the barrel assembly rotates and slides within the opening.

19. The surgical retractor of claim 16, wherein the opening in the base member includes at least one slot.

20. A surgical retractor comprising:

a retractor body;

a retractor arm including a first portion configured to operatively connect to a retractor blade and a second portion configured to operatively connect to the retractor body; and a control assembly configured to control movement of the retractor blade, the control assembly including a base member of the first portion of the retractor arm having an opening and movable between a first position and second position, a regulating member configured to control rotation of the first portion of the retractor arm and move through the opening of the base member of the first portion of the retractor arm, a connecting member cooperatively connected to the regulating member, and a barrel assembly in operative slidable engagement with the opening formed in the base member of the first portion of the retractor arm, wherein rotation of the regulating member in a selected direction moves a stem of the regulating member through the opening thereby forcing the barrel assembly to slide along the opening and the base member of the first portion of the retractor arm to pivot relative to the second portion of the retractor arm between a first position and second position, wherein the opening includes a first slot and a second slot.

* * * * *